United States Patent [19]

Szendrei et al.

[11] Patent Number: 4,511,559

[45] Date of Patent: Apr. 16, 1985

[54] BIOLOGICALLY ACTIVE POLYSACCHARIDE CONCENTRATES AND PROCESS FOR PRODUCTION OF PREPARATES CONTAINING SUCH SUBSTANCES

[75] Inventors: Kálmán Szendrei; Emil Minker; Zsuzsanna Rózsa, all of Szeged; Lehel Koch; Lajos Wolf, both of Budapest, all of Hungary

[73] Assignee: Központi Váltó-és Hitelbank Rt. InnovációAlap, Budapest, Hungary

[21] Appl. No.: 472,060

[22] Filed: Mar. 4, 1983

[30] Foreign Application Priority Data

Mar. 4, 1982 [HU] Hungary ................................. 660/82
Feb. 9, 1983 [HU] Hungary ................................. 660/82

[51] Int. Cl.$^3$ ............................................ A61K 31/715
[52] U.S. Cl. ........................................ 514/54; 424/49; 536/1.1; 536/123; 536/127; 536/128
[58] Field of Search .......................... 424/180, 49, 361; 536/1.1, 127, 128, 123

[56] References Cited

U.S. PATENT DOCUMENTS

| | | | |
|---|---|---|---|
| 2,871,235 | 1/1959 | deJilovice | 536/128 |
| 3,227,616 | 1/1966 | Van Wessem et al. | 536/128 |
| 3,374,222 | 3/1968 | Peniston | 536/127 |
| 4,119,435 | 10/1978 | Nakao et al. | 536/128 |
| 4,366,308 | 12/1982 | Soma et al. | 536/128 |

OTHER PUBLICATIONS

Aspinall et al., "Reprint from the Jour. of the Chem. Soc.", Dec. 1964, (972), pp. 5058–5063.

*Primary Examiner*—Johnnie R. Brown
*Attorney, Agent, or Firm*—Karl F. Ross; Herbert Dubno

[57] ABSTRACT

A polysaccharide-concentrate obtained from plant of the genera Cucurbitaceae, Papilionaceae, Tiliaceae, Labiate, Malvaceae, Asteraceae, Umbelliferae, Rutaceae, Chenopodiaceae, Linaceae, Rosaceae and Plantaginaceae by extraction with water and precipitation of the polysaccharide with alcohol or acetone, if desired after further purification. The polysaccharides having a molecular weight between 75,000–2,000,000, containing maximum 5% of nitrogen, maximum 5% of phosphorus (expressed in $P_2O_5$), maximum 25% of ash, minimum 30% of reducing sugar, minimum 60% of total sugar (after acidic hydrolysis, expressed as glucose) has been shown to have especially anti-inflammatory activity.

8 Claims, No Drawings

BIOLOGICALLY ACTIVE POLYSACCHARIDE CONCENTRATES AND PROCESS FOR PRODUCTION OF PREPARATES CONTAINING SUCH SUBSTANCES

The invention relates to biologically active polysaccharide concentrates having especially anti-inflammatory properties, to therapeutic or cosmetic compositions containing such substances and their production. The polysaccharide concentrates are available from starting materials of plant origin by the process of the invention.

In the practice of this invention polysaccharides are optically active heteroglycans built from monosaccharide units of furanose or pyranose structure by glycoside or ether bonds, and their basic or acidic functions as being able to link with proteins and/or peptides under special circumstances (peptidoglycans or glycoproteins). In the practice of the invention anti-inflammatory activity embraces all those activities, which are possible to be demonstrated by the carrageenan rat paw oedema test or not excluded by it. The anti-inflammatory agents which proved to be active in the rat paw oedema test may be anti-rheumatics, anti-ulcus agents, possibly in the form of creams for external use, jellies, solutions or bio-active cosmetics too.

The anti-inflammatory agents of synthetic origin, used presently in medicine, on the one hand consist of steroids, which represents many problems of tolerance, for example they often exert hormonal activity, retain sodium ions in the organism, may cause atrophies. On the other hand, use of the non steroidal inflammation inhibitors is also limited, because of their side effects. These side effects, generally characteristic of indomethacin and the acetyl salicylates, decrease the resistance of the organism, generate gastro-intestinal troubles, internal bleedings, ulcers. Because of these toxic adverse effects it was considered useful to investigate anti-inflammatory agents of natural origin. The increased intensity of the investigation is further motivated by the also expanded use of the anti-inflammatory agents for treatment of tissue oxygen delivery troubles, for example heart attacks and other tissue circulation problems and conditions of shocks. Numerous medicinal plants and compositions manufactured therefrom are used in the medicine and in cosmetics on those fields which require the presence of anti-inflammatory substances. The structure of those ingredients of the different drugs and compositions made from them, which carry the activity, is in a large part not cleared up yet. The *Chamomillae flos* e.g. is widely used in the form of tea, tea mixture, distillates (volatile oils) to cure very different illnesses. It is supposed and partially proved pharmacological activity of Chamomilla the anti-inflammatory one, and the activity on the smooth muscles. (F. Auster; J. Schäfer: Arzneipflanzen 15. 19. 21. Lieferungen: W. Spaich: Moderne phytoterapie, Hauge Verlag 1978.) The manifolded medicinal and cosmetic application of Chamomilla is orientated firstly to the treatment of the inflammatory processes of skin and mucous membranes. The treatment is carried out by means of creams, baths, inhalations, teas, in given case extracts with water or active substances incorporated into cosmetics. For internal use it is used in the form of a tea against the catarrhal and spastic illnesses of the digestive tract, the ulcerous degenerations or fissures of the mucous membrane. As a result of up to date research the anti-inflammatory activity of Chamomilla is attributed to the lipoid-like terpenoides (azulene, alpha-bisabolole, bisabolole-oxides, O. Isaak: Planta Med. 35. 118. (1979). By measuring the anti-inflammatory activity of the activity-carriers it was found that their $ED_{50}$ values are between 1465 to 3164 mg/kg. There is, however, a tremendous difference between the actual concentration of active substances in the drug or compositions and the pharmaceutical activity assigned to the active substances. [Verzárné, Petri G.: Marczal J.: Herba Hung. 15 (2) 69. (1976)]. If the designated activity carrier lipoid-like compounds are poorly soluble in water, it raises the question how could they be the most important active components of the aqueous teas. Numerous medicinal drugs or non medicinal plants are known from which the attempt to isolate the anti-inflammatory components was unsuccessful. Such are the Malva, Tilia, Plantago species, the *Linum usititassimum*, the *Trigonelle foenum-graecum*, the *Cydonia oblongara*. The aim of the invention was the isolation of such biologically active, mainly anti-inflammatory substances group from plants already investigated or as a medicinal drug obtained from plants which can be isolated easily and which may be utilized for the manufacture of pharmacological or cosmetic compositions, which show a comparable anti-inflammatory activity with the presently used synthetic compositions and simultaneously have much lower toxicity. According to the invention the biologically active substances are available by processing the plants belonging to the following genera: Cucurbitaceae, Papilionaceae, Tiliaceae, Labiate, Malvaceae, Asteraceae, Umbelliferae, Rutaceae, Chenopodiaceae, Linaceae, Rosaceae and Plantaginaceae. From the above mentioned genera the *Chamomillae flos, Tiliae flos, Althaeae radix, Malvae folium et flos, Malvae arboraea herba, Plantaginis folium, Psyllii semen, Cydoniae semen, Lini semen, Trigonella foeni-graeci semen, Cucurbitae maximae fructus, Kitaibela vitifoliae herba, Daucus carottae radix, Beta vulgaris convarietas conditivae radix* or their mixture are preferred. A polysaccharide fraction having a significant anti-inflammatory activity can be isolated from the enumerated plant starting materials as well from the fresh, as well from the re-hydrated dried drugs, under circumstances different from the usual circumstances of extraction. Extraction is carried out with a little water at ambient temperature. Incidentally this polysaccharide fraction obtained by precipitation and further purification can be transformed into such a concentrate which is incorporable into pharmaceutical or cosmetic compositions.

The polysaccharides of plant origin according to the invention can be characterised by:
a. having a molecular weight between 75,000 and 2,000,000,
b. containing maximum 5% nitrogen (Wagner-Parness micro-Kjeldahl method),
c. maximum 5% of phosphorus expressed in $P_2O_5$ (molibdenate - Eiconogene reagent),
d. minimum 30% of reducing sugar (after acidic hydrolysis determined by o-toluidine),
e. minimum 60% of total sugar (determined by the phenol-sulfuric acid method and expressed as glucose),
f. maximum 25% of ash,
g. analyzing on a column filled with Sephadex G-75 molecular sieve they are substantially free from any substance having a lower molecular weight than 75,000, h. after acidic hydrolysis there result members selected from the group consisting of glucose, galactose, xylose, rhamnose, arabinose and uronic acid, with the proviso that they contain at least two of said members, i. studied by the rat paw carrageenan oedema test they exhibit an anti-inflammatory activity of the same order as the phenylbutazone or indomethacin, k. their $LD_{50}$ value in mice per os is greater than 3000 mg/kg or in rat greater than 2000 mg/kg.

The polysaccharide extracted from the *Cucurbita maximae fructus* has the following characteristics: molecular weight greater than 300,000, nitrogen content maximum 3%, phosphorus content (expressed as $P_2O_5$) maximum 5%, ash content maximum 20%, reducing sugar content minimum 30%, total sugar content minimum 60%, after acidic hydrolysis it decomposes into mainly glucose, galactose and uronic acid, its anti-inflammatory activity at 10 mg/kg dose on the rat paw carrageenan oedema test is at least 50%.

Similarly preferred is the polysaccharide from the *Trigonella foenum-graecum*, which has a molecular weight greater than 100,000, its nitrogen content is maximum 3%, phosphorus content maximum 4% (expressed as $P_2O_5$) ash content maximum 5%, reducing sugar content minimum 50%, total sugar content minimum 70% (after acidic hydrolysis/expressed as glucose), it decomposes mainly into galactose and mannose, its anti-inflammatory activity at 10 mg/kg dose on the rat paw carrageenan oedema test is at least 40%. The polysaccharide concentrates according to the invention are obtained by a procedure in which the drug, freshly collected or dried or previously treated with an organic solvent, at a temperature between 0°–40° C., advantageously after a previous disintegration or simultaneously with a disintegration with water is treated for a period of 1–24 hours, the solid is separated and, after the precipitation of the proteins present in the aqueous phase, the polysaccharide concentrate is precipitated by adding an alcohol of 1–3 carbon atoms, or acetone, or cations of 1–3 valence, which precipitate is separated from the aqueous phase and further purified, if desired. The aqueous extraction is carried out with a quantity of water 1–20 times related to the weight of the drug. The fresh plant or the dried and with water treated plant is occasionally ground or disintegrated, the grist is pressed afterwards, the residue is treated with water again, then pressed anew. The polysaccharide concentrate is precipitated from the aqueous solution advantageously by adding methanol or ethanol, then purified by dissolving it in water again and precipitating and/or extracting it with an alcohol of 1–3 carbon atoms. To separate the protein fraction present in the aqueous solution, it is heated up to 40°–80° C. It is preferred to disintegrate the drug in an aqueous medium. In the case of using a dried drug, dry or wet disintegration is applicable. The aqueous extraction can be carried out without disintegration, for example in the case of coarsely ground roots. The aqueous extraction can be accomplished by cooling at a temperature about +4° C., but in certain cases a temperature above 30° C. was beneficial. The continouos processing is preferred where as the starting material is wetly ground, then pressed at low or high pressure, possibly repeatedly, and the pressed material occasionally treated with water anew. The juice pressed or extracted and separated by pressing, contains the polysaccharide fraction which is the desired end product. The concentrate is precipitated from the aqueous medium by an alcohol of 1–3 carbon atoms or acetone, or by the use of cations of 1–3 valence. The individual methods for precipitation can be combined with each other. The weight of the obtainable polysaccharide concentrate is between 0.1–10 weight % relating to the dry matter content of the starting material. Further possibility for processing is the extraction of the ground plant material by a quantity of water 1–20 times as much as its weight, the heat treatment of the extract at 60° C., the purification of the heat-treated extract by centrifuge or filtration, the precipitation of the polysaccharides from the solution by alcohol 2–3 times of its volume, and after 24 hours allowing to stand, the separation of the precipitate from the mother liquor by centrifuge or filtration, and washing it with an alcohol. The purification of the precipitated raw polysaccharide concentrate is accomplished by dissolving the wet material in water of ten times volume of its weight, heating it to 75° C., separating the deposited materials by centrifuge and mixing the supernatant with alcohol 3 times its volume. After a 24 hours rest the deposited solid is separated by centrifuge and filtration, washed with alcohol, and dried in vacuo maximum at 40° C.

Further purification can be accomplished by dissolving the dried product at 50°–75° C. in water 30–40 times its weight, clarifying it by centrifuge and filtering it at 3–10 atm. pressure through such a membrane, which lets through the substances of a molecular weight of less than 75,000, then precipitating the polysaccharides by alcohol from the solution remained on the large molecular weight side of the membrane. The polysaccharide is precipitable from the aqueous solution by acetone as well.

The anti-inflammatory composition according to the invention comprises polysaccharides isolated by the process referred to and in given case a non-steroidal anti-inflammatory agent, especially indomethacin or acetyl-salycilic acid, together with a pharmaceutically acceptable ingredient or carrier. The pharmaceutical composition is suitable to administer per os or parenterally. As to its form it may be a tablet, dragée, capsule, infusion, emulsion, injection, solution, suppositorium, implantate, or externally applicable solution, mucilage, cream, ointment or jelly. The anti-inflammatory composition is suitable for pharmaceutical or cosmetic purposes, and is manufactured by mixing the above described polysaccharide concentrate together with the ingredients and/or carriers usual for the preparation of pharmaceutical or cosmetic compositions and preparing thus an inflammation inhibiting composition in a known manner.

The anti-inflammatory activity of the polysaccharide concentrates produced according to the invention was investigated on the rat paw carrageenan oedema test according to Winter et al. [Proc. Soc. Exp. Biol. Med. 111. 544. (1962)]. The concentrate has a significant specific activity and in connection with its advantageous anti-inflammatory activity it posseses a remarkably low toxicity. Comparing to the 45% inhibition of the 100 mg/kg dose of phenylbutazone used as a standard, the concentrates according to the invention in a similar dose show an inhibition of 70–80%. Similar favorable effect is demonstrated in comparison with the indomethacin.

The biological activity may be simply demonstrated by dissolving the polysaccharide concentrate in 0.5% concentration in water. The obtained solution is suitable for throat gargling, mouth gargling (pharyngitis, gingivitis), eye rinsing (coniunctivitis), for rinsing, at inflammatory illnesses of the outer auditory meatus and by the application of a wet gauze, for compress. A hip bath made from polysaccharides is beneficial for treatment of fissura ani, nodus hemorrhoidalis, vaginits, vulvovaginitis, fissura mammae and as compress for dermatitis.

The isolation and pharmacological activity of the polysaccharides according to the invention is illustrated by the following examples:

EXAMPLE 1

200 g of fresh *Chamomillae flos* with 400 ml of water was homogenised by wet disintegration then allowed to rest at 20° C. for 20 hours. The aqueous phase was separated by centrifuge, the remaining solid was removed by filtration. 1000 ml of methanol was given afterwards during continuous stirring to the aqueous extract, the precipitated solid was filtered, washed with methanol and dried, there by 0.3 g polysaccharide concentrate was obtained. If 1000 ml ethanol was used in the place of methanol, the obtained product was 0.32 g of concentrate.

EXAMPLE 2

200 g of dried *Chamomillae flos* was disintegrated together with 1000 ml of water, then kept at 20° C. for 2 hours. The aqueous part was purified by centrifuge and filtration, then 2500 ml of methanol was added, and the deposited solid filtered. The precipitate was washed with methanol, and 2.12 g of polysaccharide was obtained.

EXAMPLE 3

200 g of fresh *Chamomillae flos* was ground, and the grist pressed. The residue was treated with 200 ml of water at 20° C. for 1 hour, and pressed again. The united aqueous phases were filtered, then 600 ml of methanol was added while stirring. The precipitated solid was filtered, washed with methanol and dried. 0.26 g of polysaccharide was obtained.

EXAMPLE 4

The procedure is the same as in the example 3 with the difference, that in the place of 2500 ml of methanol 2000 ml of acetone was added to the aqueous extract. The precipitated solid was filtered and washed with acetone and dried. The yield was: 2.43 g of polysaccharide concentrate.

EXAMPLE 5

200 g of dried *Tiliae flos* was disintegrated together with 1500 ml water, then kept at 20° C. for 3 hours. After filtration the aqueous extract was processed according to example 1 and 1.86 g of polysaccharide was obtained.

EXAMPLE 6

200 g of fresh *Chamomillae flos* was processed according to Example 3. The yield was 0.62 g of polysaccharide concentrate.

EXAMPLE 7

2000 g of dried *Tiliae flos* was ground and the grist was treated with 5000 ml of 60% methanol at 20° C. for 24 hours. The solid material was separated by pressing and filtration. The drying was carried out at ambient temperature. 28 l of water was added to the dried material, then it was stirred at 20° C. for 24 hours, then the aqueous phase was separated by centrifuge. 56 l of ethanol was added to the aqueous phase while stirring, the precipitated solid was filtered, washed with ethanol and dried. 47.18 g of polysaccharide concentrate was obtained this way, which was dissolved in 500 ml water, and purified by precipitating it with 1000 ml of methanol. The purified polysaccharide concentrate weighed 32.64 g.

EXAMPLE 8

7.8 g of fresh *Cydoniae semen* was soaked in 50 ml of water at +4° C. for 24 hours. It was then filtered, and 100 ml of methanol was added under stirring to the aqueous phase, the precipitated solid was filtered, washed with methanol and dried. The yield was 2.4 g of polysaccharide concentrate.

EXAMPLE 9

200 g of dried *Lini semen* was extracted by means of 500 ml of water at +36° C. for 2 hours. After filtration, 1000 ml of methanol was added to the aqueous extract, the precipitated solid filtered, washed with methanol and dried. The yield was 6.79 g of polysaccharide concentrate.

EXAMPLE 10

200 g of fresh *Alteae radix* was cut coarse and treated with 400 ml of water at +20° C. for 4 hours. The aqueous phase was separated by centrifuge, then under stirring 800 ml of ethanol was added to it, the precipitated solid was filtered, washed with ethanol and dried. 0.34 g of polysaccharide concentrate was obtained.

EXAMPLE 11

32 kg of fresh *Kitaibela vitifoliae herba* was disintegrated in the presence of 30 l water, then pressed at 230 atm pressure. 50 liters of pressed juice was obtained, which was heated to 75° C., and the precipitated proteins were removed by centrifuge. The supernatant was concentrated into 2 liters at reduced pressure, 14 l of methanol was added under stirring to the concentrate, and the mixture was allowed to rest for 24 hours. The precipitated product was then isolated by centrifuge, washed with methanol and dried at 60° C. 87.0 g of polysaccharide concentrate was obtained.

EXAMPLE 12

1 kg of *Trigonella foeni-graeci semen* was disintegrated by a hammer mill provided with a 2 mm sieve insert, the ground material was then stirred with 8.7 l of water at +23° C., for 6 hours. The aqueous extract was then separated in a centrifuge, the obtained 5 l solution was heated to 72° C., and the protein precipitated removed by filtration. 5 l of n-propanol was then added to the filtered juice under stirring, then it was allowed to rest for 13 hours and centrifuged afterwards. The sediment was mixed with 0.5 l of propanol, disintegrated in an aqueous medium, then centrifuged again. The sediment was then dried at 45° C. under reduced pressure. The yield was 50.0 g of polysaccharide concentrate.

EXAMPLE 13

1 kg of *Cucurbita maximae fructus* was cleared from its skin and seeds, mixed with 1.5 liter of water at 20° C., mashed in a disintegrator, then pressed in a hydraulic press at 130 atm. The pressed juice was filtered through a K-5 Seitz filter. 1500 ml of filtrate was obtained, which was then concentrated at 40° C. under reduced pressure to 40% of dry matter content. 300 ml of ethanol of 96% concentration was added under stirring to the 140 ml concentrate. The precipitate containing mixture was then allowed to rest for 12 hours at room temperature. The sediment was separated by centrifuge, then triturated with 100 ml of ethanol of 96% concentration, filtered and dried under reduced pressure, 3.0 g of polysaccharide concentrate was obtained.

EXAMPLE 14

200 g of dried *Malvae folium* was extracted with 1 liter of water. The aqueous extract was allowed to rest for 2 hours, then the aqueous phase was separated by pressing and by centrifuging and filtering the pressed juice. 2 l of methanol was added to the clean aqueous extract under stirring, the precipitated solid was filtered and washed with methanol. The yield was 2.0 g of polysaccharide concentrate. If as starting material in the place of the dried *Malvae folium* the same quantity of dried and ground *Malvae flos* was used, 3.5 g of polysaccharide concentrate was obtained.

Also the same way, starting from 200 g of dried and ground *Malvae arborae herba*, 1.0 g of polysaccharide concentrate was obtained.

EXAMPLE 15

200 g of dried and ground *Plantaginis folium* was processed according to Example 14 and 0.5 g of polysaccharide concentrate was obtained.

EXAMPLE 16

200 g of dried *Psyllii semen* was extracted with 500 ml of water, and further processed according to Example 14. 10.0 g of polysaccharide concentrate was obtained.

EXAMPLE 17

200 g of dried *Tiliae flos* was extracted according to Example 5 and 30 g of $Ba(OH)_2$ was added to the clean aqueous extract. The deposited precipitate was filtered, washed with alcohol and an aqueous sodium-sulfate solution. 2.3 g of polysaccharide concentrate was obtained.

The above Example repeated, but in the place of $Ba(OH)_2$ 45 g of $(NH_4)_2SO_4$ was added. The precipitate was filtered and washed with alcohol. The yield was 2.0 g of polysaccharide concentrate.

EXAMPLE 18

The mixture of 200 g dried and ground *Malvae flos* and 200 g of dried and ground *Psyllii semen* was extracted with 2 l of water and further processed according to Example 14. 2.7 g of polysaccharide concentrate was obtained.

EXAMPLE 19

10 kg of *Cucurbita maximae fructus*, which contained 15% of dry matter, 4% of reducing and 5% of non-reducing sugar, and 3% of polysaccharides, was halved and the seeds removed. The starting material was mashed by means of a disintegrator into a coarse pulp, then mixed with 10 l of water. The mixture was heated under stirring to 35° C., stirred one hour, there after 6 hours of standing it is pressed; 12 liters of pressed juice were obtained. The residue was suspended in 10 l of water, stirred for one hour, then pressed, and another 12 liters of pressed juice were obtained.

The two juices were united, heated to 60° C. under stirring, then centrifuged and the protein sediment discarded. The centrifuged solution was filtered through a Seitz K-5 filter, the solid was discarded. The clear solution was concentrated under reduced pressure at 60° C. temperature to 10–20% dry matter content. The concentrate cooled to room temperature was then centrifuged, and the precipitate was discarded. To the supernatant 3 times of its volume of methanol was then added under vigorous stirring, and the mixture with the precipitate was allowed to rest at room temperature for 24 hours. The supernatant was decanted and discarded. The sedimentous solution was then centrifuged, and the sediment was disintegrated in 500 ml of methanol, and centrifuged again. The sediment obtained by centrifuge was twice more washed with methanol. After the third desintegration of the sediment, the sediments containing solution was transferred to a vacuum filter, and the mother liquor filtered off. The wet filter cake was a white precipitate. This was disintegrated in distilled water 10 times of its weight, the solution was heated to 75° C. and centrifuged while keeping warm. 3 times of its volume methanol was then added under stirring to the purified solution, and allowed to stand 24 hours at room temperature. It was centrifuged afterwards, the obtained precipitate was disintegrated in 300 ml methanol and centrifuged again. The washing with methanol and the disintegration was then repeated twice more, and after the third purifying operation the precipitate was filtered on a vacuum filter, and the filtered deposit was dried in vacuum at 40° C. The yield was 21.1 g of white powder-like polysaccharide concentrate.

For the sake of further purification the polysaccharide was dissolved in 600 ml of distilled water at 50° C., allowed to stand one hour, then centrifuged. The supernatant was filtered at 5 atm pressure in a membrane filter, which retained those substances having higher molecular weight than 75,000 (Diaflo XM 300, Amicon Co. USA). The solution remained on the high molecular weight side of the membrane was diluted to 3 times its volume with distilled water, then pressed through the membrane again. Finally the solution remained on the high molecular weight side of the membrane was centrifuged, and 3 times of its volume of methanol was added to the supernatant under stirring. It was then allowed to stand 24 hours at room temperature. The precipitated solid was filtered in a vacuum filter, and was dried at 40° C. in vacuo. The weight of the purified polysaccharide was 13.2 g.

EXAMPLE 20

10 kg of *Trigonella foeni-graeci semen* was ground in a hammer-mill provided with a 3 mm sieve insert. 40 l of water was added to the grist at 35° C. and it was stirred for 6 hours, then the solid was removed by a separator. The extraction was then repeated with 30 l of water at 35° C. by stirring for 3 hours. The united aqueous extracts were heated to 60° C., then purified by centrifuge and filtration. 2 times of its volume ethanol of 96% concentration was added to the aqueous phase under vigorous stirring. It was then further processed according to Example 19 and 180 g of polysaccharide concentrate was obtained. After acidic hydrolysis galactose and mannose were detectable.

The polysaccharide concentrates according to Examples 1–20 were passed through a column filled with Sephadex G-75 molecular sieve, and analyzed.

The analytical data are the following:
molecular weight: 75,000–2,000,000 they contain maximum 5% of nitrogen and 5% of phosphorus expressed in $P_2O_5$
they contain maximum 25% of ash
they contain minimum 60% total sugar expressed in glucose, and within total sugar minimum 30% of reducing sugar
after acidic hydrolysis they contain members selected from the group consisting of glucose, galactose, xylose, rhamnose, arabinose and uronic acid at least two members or a mixture thereof
tested by the rat paw carrageenan oedema test they exert an anti-inflammatory activity about the same order as the indomethacine or phenylbutazone
their $LD_{50}$ in rat, per os is greater than 3000 mg/kg.
Analytical methods used:
Phosphorus content: Peac-Tracey: Moderne Methoden der Pflanzenanalyse Volume IV, p. 308.
Reducing sugar content: R. Richterich: Klinische Chemie 1968, p. 233, Carger Ed. Basel-New York
Total sugar content: M. Dubois: Anal. Chem. 28. p. 35, 1956.

EXAMPLE 21

An anti-inflammatory suppositorium is prepared from the purified polysaccharide concentrate according to Example 19. It was micronized to a grain fineness between 1–5 microns. 0.5 g micronized polysaccharide was then mixed into a suppositorium of 3 g, moulded at 40° C., which was consisted of *Adeps solidus* (lanolin) containing 5 to 30% of *Butirum cacao* (Pharmacopea Hungarica VI. Ed. VII. Tom. 1.).

EXAMPLE 22

An externally applicable jelly was prepared from a 3% aqueous Carbopol 934 solution which was adjusted to pH 7.0 by 1 N sodium hydroxyde, and 3% of polysaccharide concentrate according to Example 19. The latter was dissolved in the aqueous phase prior to use. The jelly was conserved by 0.5% of sorbic acid or 0.1% of Nipagin.

EXAMPLE 23

An ointment was prepared using the conserving agents according to Example 20. Both were dissolved in 5% concentration in water and the solution was mixed by 1:1 ratio with 1000 g of Unguentum emulsificans (Composition: 100 g of carboxethane-stearate, 100 g of paraffin, 300 g of cetyl-alcohol-stearete, 500 g of vaselinum album) and homogenized.

EXAMPLE 24

A per os pharmaceutical suspension was prepared using 5 g of purified polysaccharide according to Example 20 which was dissolved in 100 g of water. 0.12 g of sorbic acid, 2.8 g of magnesium oxide, 8 g of aluminium-hydroxide, 60 g of methylcellulose-hydrogel and 20 g of sorbite were added, and the mixture was filled up with distilled water to 200 g.

EXAMPLE 25

A tablet for oral use was prepared using 0.25 g of polysaccharide concentrate according to Example 19 which was pressed into tablet together with Granulatum simplex having the following composition:
60 parts of lactose
16 parts of saccharose
20 parts of potato starch
2 parts of talcum
2 parts of magnesium-stearate.

The anti-inflammatory activity of the polysaccharide concentrate according to the invention was investigated intraperitoneally on rat according to the paw carrageenan oedema test. Simultaneously the $LD_{50}$ values of the polysaccharide concentrates (i.p.) were determined.

| Polysaccharide concentrate | Dose mg/kg | Inhibiton % | $LD_{50}$ mg/kg |
|---|---|---|---|
| Chamomillae flos, fresh (example 1) | 50 | 74.1 | >1500 |
| Chamomillae flos, dried (example 2) | 100 | 71.7 | >1500 |
| Tiliae flos, dried (example 7) | 100 | 80.3 | >1000 |
| Altheae radix, fresh (example 10) | 100 | 54.2 | >1500 |
| Cydoniae semen, fresh (example 8) | 100 | 52.5 | >1000 |
| Lini semen, dried (example 9) | 100 | 43.8 | >1000 |
| Phenylbutazone | 100 | 45.0 | 215 |

The anti-inflammatory activity of the prepared polysaccharide concentrates was determined in comparison to the indomethancin as well using the rat paw carrageenan oedema test. The polysaccharide sample was intraperitoneally injected one hour before the inflammation inducing carrageenan. As reference standard per os applied indomethacin was used, which was suspended in 1% methylcellulose solution, and given through a gastric tube into the stomach one hour prior to the administration of Carrageenan to CFY rats and CFLP mice. The dosage was the same during the toxicity studies as well. The anti-inflammatory activity of the individual polysaccharides, their $LD_{50}$ values and therapeutic indexes are illustrated in the following table (intraperitoneal dosage in rats).

| Polysaccharide concentrate | Anti-inflammatory activity $ED_{50}$ mg/kg | | $LD_{50}$ mg/kg | Therapeutic index $LD_{50}/ED_{50}$ | |
|---|---|---|---|---|---|
| | 2 hours | 5 hours | | 2 hours | 5 hours |
| Cucurbita (Example 19) | 0.51 | 0.37 | 112 | 219.6 | 302.7 |
| Tilia (Example 7) | 2.83 | 2.20 | 150 | 53.0 | 68.2 |
| Trigonella (Example 20) | 2.19 | 1.17 | 200 | 91.3 | 170.9 |
| Indomethacin (p.o.) | 3.14 | 2.20 | 32 | 10.2 | 14.5 |

The activities of some polysaccharides prepared according to the invention compared to the indomethacin are illustrated on the following table:

| Polysaccharide concentrate | Compared activites $ED_{50}$, indomethacin/$ED_{50}$, polysaccharide | |
|---|---|---|
| | 2 hours | 5 hours |
| Cucurbita | 6.16 | 5.95 |
| Tilia | 1.11 | 1.00 |
| Trigonella | 1.43 | 1.88 |

The activities of some polysaccharides produced according to the invention compared to some widely used anti-inflammatory agents are represented on the following table:

| Polysaccharide concentrate | Dose mg/kg | Anti-inflammatory activity % | LD$_{50}$ mg/kg | Dose/LD$_{50}$ ratio |
|---|---|---|---|---|
| Cucurbita | 10 | 54 | 214 | 0.046 |
| Trigonella | 10 | 40 | 250 | 0.040 |
| Indomethacin (p.o.) | 10 | 51 | 17 | 0.580 |
| Phenylbutazone (p.o.) | 90 | 40 | 470 | 0.190 |
| Aspyrine (p.o.) | 400 | 36 | 1200 | 0.330 |

The polysaccharides produced according to the invention show significant effectivity on chronic inflammation models too, for example on adjuvans arthritis in rat, at intraperitoneal treatment for 3 weeks:

| Polysaccharide concentrate | Dose mg/kg | Anti-inflammatory activity % |
|---|---|---|
| Cucurbita | 50 | 46 |
| Cucurbita | 10 | 46 |
| Trigonella | 50 | 37 |
| Phenylbutazone | 50 | 64 |

Another important result of the pharmacological studies is that the investigated polysaccharide concentrates as anti-inflammatory substances presumably act by influencing the kinine-phase of the inflammation. It is known that the developement of the carrageenan oedema exhibits 3 phases, i.e. the amine (histamine, serotonine), the kinine (bradykinine) and the prostaglandine (PG) phases. To develop the PG phase 5 hours are required from the injection of the inflammation inducing carrageenan. The polysaccharide concentrates of this invention do not inhibit the PG synthesis, as they have no ulcerogenity. The importance of this should be emphasised because the non steroidal anti-inflammatory and anti-rheumatic agents develop their activity by the inhibition of the PG syntethase, and can also develop ulcers in the stomach or intestines. If these non steroid anti-inflammatory agents, especially the indomethacin and the acetylsalicylic acid derivatives are combined with the polysaccharides of this invention, the ulcerogenic activity of the former agents could be prevented. According to the toxicological studies the acute toxicity of the polysaccharide concentrates in rat and mice can be characterized by a rather steep dose activity curve. 8 days of intraperitoneal dosage with the 1/3d or 1/10th of the acute dose practically does not cause mortality either in rats or in mice.

What we claim is:

1. A polysaccharide composition obtained from a plant extract and having an anti-inflammatory activity, said polysaccharide being characterized by:
   (a) having a molecular weight between 75,000 and 2,000,000;
   (b) containing a maximum of 5% nitrogen;
   (c) containing a maximum of 5% phosphorus expressed as $P_2O_5$;
   (d) containing a maximum of 25% ash;
   (e) containing a minimum of 30% reducing sugar;
   (f) containing a minimum of 60% of total sugar after acidic hydrolysis, expressed as glucose;
   (g) substantial freedom from substances with a molecular weight below 75,000 on analysis on a column filled with Sephadex G-75 molecular sieve;
   (h) yielding members selected from the group consisting of glucose, galactose, xylose, rhamnose, arabinose and uronic acid and containing at least two of said members upon acid hydrolysis;
   (i) exhibiting an anti-inflammatory activity of the same order as phenylbutazone or indomethacin as measured by the rat paw carrageenin oedema test; and
   (k) their LD$_{50}$ value in mouse per os is greater than 3000 mg/kg and in rat greater than 2000 mg/kg.

2. A polysaccharide according to claim 1 obtained from a plant belonging to the following genera: Cucurbitaceae, Papilionaceae, Tiliaceae, Labiate, Malvaceae, Asteraceae, Umbelliferae, Rutaceae, Chenopodiaceae, Linaceae, Rosaceae, or Plantaginaceae.

3. A polysaccharide according to claim 1 obtained from at least one of the following plants: *Chamomillae flos, Tiliae flos, Altheae radix, Malvae folium et flos, Malvae arborae herba, Plantaginis folium, Psyllii semen, Cydoniaea semen, Lini semen, Trigonella foeni-graeci semen, Cucurbita maximae fructus, Kitaibela vitifoliae herba, Daucus carottae radix,* and *Beta vulgaris convarietas conditivae radix.*

4. A polysaccharide according to claim 1 obtained from *Cucurbita maxima,* having a molecular weight greater than 300,000, containing maximum 3% of nitrogen, maximum 5% of phosphorus expressed as $P_2O_5$, maximum 20% of ash, minimum 30% of reducing sugar, minimum 60% of total sugar, and after acidic hydrolysis they decompose mainly into glucose, galactose and uronic acid, and exhibiting at least 50% anti-inflammatory activity in the rat paw carrageenin oedema test.

5. A polysaccharide according to claim 1 obtained from *Trigonella foeni-graeci semen,* having a molecular weight greater than 100,000 containing maximum 3% of nitrogen, maximum 4% of phosphorus expressed in $P_2O_5$, maximum 5% of ash, minimum 50% of reducing sugar, minimum 70% of total sugar, and after acidic hydrolysis they decompose mainly into galactose and mannose, and exhibiting at least 40% anti-inflammatory activity in rat paw carrageenin oedema test.

6. A pharmaceutical composition having anti-inflammatory activity comprising of a polysaccharide concentrate according to claim 1, a non-steroidal anti-inflammatory agent, selected from the group which consists of indomethacin, acetyl-salicylic acid or a derivative thereof, together with a pharmaceutically acceptable pharmaceutical carrier.

7. A cosmetic composition, comprising a cosmetically effective amount of a polysaccharide according to claim 1 together with a cosmetically acceptable carrier.

8. A method of treating an inflammatory condition which comprises administering to a susceptible subject an anti-inflammatory effective amount of a polysaccharide as defined in claim 1.

* * * * *